(12) United States Patent
Williams

(10) Patent No.: US 7,699,995 B2
(45) Date of Patent: Apr. 20, 2010

(54) WATER TREATMENT METHOD

(75) Inventor: Terry Michael Williams, Lower Gwynedd, PA (US)

(73) Assignee: Rohm and Haas Company, Philadelphia, PA (US)

( * ) Notice: Subject to any disclaimer, the term of this patent is extended or adjusted under 35 U.S.C. 154(b) by 480 days.

(21) Appl. No.: 11/729,667

(22) Filed: Mar. 29, 2007

(65) Prior Publication Data

US 2007/0251890 A1 Nov. 1, 2007

Related U.S. Application Data

(60) Provisional application No. 60/801,554, filed on May 18, 2006, provisional application No. 60/790,439, filed on Apr. 7, 2006.

(51) Int. Cl.
*C02F 1/50* (2006.01)

(52) U.S. Cl. .................. 210/764; 422/28; 508/271; 514/372

(58) Field of Classification Search .................. 210/764
See application file for complete search history.

(56) References Cited

U.S. PATENT DOCUMENTS

| 3,761,488 | A | | 9/1973 | Lewis et al. |
| 4,105,431 | A | | 8/1978 | Lewis et al. |
| 4,150,026 | A | | 4/1979 | Miller et al. |
| 4,241,214 | A | | 12/1980 | Miller et al. |
| 4,975,109 | A | * | 12/1990 | Friedman et al. ............ 504/122 |
| 5,028,620 | A | | 7/1991 | Hsu |
| 5,457,083 | A | * | 10/1995 | Muia et al. .................. 504/128 |
| 5,466,818 | A | | 11/1995 | Petigara |
| 6,361,788 | B1 | | 3/2002 | Antoni-Zimmermann et al. |
| 6,951,618 | B2 | * | 10/2005 | Rossmoore ................. 210/755 |
| 7,208,511 | B2 | * | 4/2007 | Williams et al. ............ 514/372 |
| 7,560,476 | B2 | * | 7/2009 | Heer et al. .................. 514/372 |

FOREIGN PATENT DOCUMENTS

| EP | 0676140 | 10/1995 |
| EP | 0773282 | 5/1997 |
| EP | 0777966 | 6/1997 |
| JP | 2002193712 A * | 7/2002 |
| WO | WO 02/36503 | 5/2002 |

OTHER PUBLICATIONS

Rohm and Haas Company; For Preservation of Latex Emulsions, Mineral Slurries, Dispersed Pigments and Related Products; Kordek LX5000; Dec. 2002.

Rohm and Haas Company; For Preservation of Latex Emulsions, Mineral Slurries, Dispersed Pigments and Related Products; Kordek MLX; Dec. 2002.

* cited by examiner

*Primary Examiner*—Peter A Hruskoci
(74) *Attorney, Agent, or Firm*—Kenneth Crimaldi

(57) ABSTRACT

A method for treating water in a closed cooling system, having a pH of at least 7 and a temperature of at least 25° C., by adding a composition comprising 2-methyl-4-isothiazolin-3-one; wherein the composition is substantially free of non-aqueous solvents, volatile organic compounds and halogenated biocides; and wherein 2-methyl-4-isothiazolin-3-one is present in an amount sufficient to produce in the water a 2-methyl-4-isothiazolin-3-one concentration from 15 ppm to 500 ppm.

5 Claims, No Drawings

WATER TREATMENT METHOD

This application claims the benefit of priority under 35 U.S.C. §119(e) of U.S. Provisional Patent Application No. 60/801,554 filed on May 18, 2006 and U.S. Provisional Application Ser. No. 60/790,439 filed on Apr. 7, 2006.

This invention relates to a method for treating water in a closed cooling water system with a biocide composition.

One of the known uses of isothiazolone biocides is treatment of water cooling systems, as disclosed in U.S. Pat. No. 3,761,488. However, the isothiazolone biocide most frequently used in commercial water cooling systems is a 3:1 mixture of 5-chloro-2-methyl-4-isothiazolin-3-one and 2-methyl-4-isothiazolin-3-one, respectively. This mixture has several disadvantages, including the relative instability of 5-chloro-2-methyl-4-isothiazolin-3-one at high pH and high temperatures. Other biocide formulations used in cooling water systems are disadvantageous for the same reason, and also due to the presence of non-aqueous solvents, salts and volatile organic compounds in the biocide formulation.

The problem addressed by this invention is to provide a method of treating water in a closed cooling system that does not suffer from the disadvantages discussed above.

STATEMENT OF THE INVENTION

The present invention is directed to a method for treating water in a closed cooling system, having a pH of at least 7 and a temperature of at least 25° C., by adding a composition comprising 2-methyl-4-isothiazolin-3-one; wherein the composition is substantially free of non-aqueous solvents, volatile organic compounds and halogenated biocides; and wherein 2-methyl-4-isothiazolin-3-one is present in an amount sufficient to produce in the water a 2-methyl-4-isothiazolin-3-one concentration from 15 ppm to 500 ppm.

The present invention is further directed to a method for control of mycobacteria (gram positive, acid-fast bacteria) in an in-use metalworking fluid system by adding 2-methyl-4-isothiazolin-3-one.

DETAILED DESCRIPTION OF THE INVENTION

"MI" or "MIT" is 2-methyl-4-isothiazolin-3-one, also referred to by the name 2-methyl-3-isothiazolone. "CMI" or "CMIT" is 5-chloro-2-methyl-4-isothiazolin-3-one, also referred to by the name 5-chloro-2-methyl-3-isothiazolone.

As used herein, the following terms have the designated definitions, unless the context clearly indicates otherwise. The term "microbicide" refers to a compound capable of inhibiting the growth of or controlling the growth of microorganisms at a locus; microbicides include bactericides, fungicides and algicides. The term "microorganism" includes, for example, fungi (such as yeast and mold), bacteria and algae. The term "locus" refers to an industrial system or product subject to contamination by microorganisms. The term "closed cooling system" refers to a system containing water used for industrial cooling applications which is not open to evaporation and in which the water loss is less than 5% of the recirculation rate. The following abbreviations are used throughout the specification: ppm=parts per million by weight (weight/weight), mL=milliliter, AI=active ingredient, i.e., total amount of isothiazolones. Unless otherwise specified, temperatures are in degrees centigrade (° C.), and references to percentages are by weight.

The composition used in the present invention preferably contains from 20% to 95% water, and from 5% to 80% MI, but is substantially free of non-aqueous solvents, i.e., it contains less than 2% of such solvents, alternatively less than 1%, alternatively less than 0.5%, alternatively less than 0.1%. The composition is substantially free of volatile organic compounds, as defined by EPA regulations, i.e., it contains less than 2% of such compounds, alternatively less than 1%, alternatively less than 0.5%, alternatively less than 0.1%. The composition is substantially free of halogenated biocides, i.e., it contains less than 0.5% of such biocides, alternatively less than 0.1%, alternatively less than 100 ppm, alternatively less than 50 ppm. Halogenated biocides include, e.g., CMI, which is often present together with MI in commercial biocides; 2-bromo-2-nitro-1-propane-1,3-diol (BNPD); and 2,2-dibromo-3-nitrilopropionamide (DBNPA). In one embodiment of the invention, the composition is substantially free of all biocides other than MI. In one embodiment, the composition is substantially free of metals, i.e., it contains less than 0.4% of metal ions, alternatively less than 0.2%, alternatively less than 0.1%. In one embodiment of the invention, when the composition is described as being substantially free of certain ingredients, the cooling water is substantially free of these ingredients, i.e., they are not added separately to the cooling water.

The composition may be used with corrosion inhibitors including, e.g., nitrites, chromates, molybdates, phosphates, zinc salts, azoles and phosphonates, which may be added separately to the cooling water. The metals present in corrosion inhibitors may be present in the cooling water in amounts that exceed those produced by any trace metals in the composition of this invention.

The composition may also be used with scale inhibitors, including, e.g., polycarboxylic acids, such as polyacrylic acids, polymaleic acids, and polyaspartic acids, or phosphates or phosphonates. Scale inhibitors may be added separately to the cooling water at use levels of less than 1 ppm, less than 10 ppm, or less than 100 ppm. Metals present in scale inhibitors may also exceed the amounts provided by the composition of this invention.

In one embodiment of the invention, the MI concentration in the cooling water is at least 20 ppm, alternatively at least 25 ppm, alternatively at least 30 ppm, alternatively at least 40 ppm, alternatively at least 50 ppm, alternatively at least 60 ppm; preferably the MI concentration is no more than 300 ppm, alternatively no more than 250 ppm, alternatively no more than 200 ppm, alternatively no more than 150 ppm, alternatively no more than 125 ppm.

In one embodiment of the invention, the pH of the cooling water is at least 7.5, alternatively at least 8, alternatively at least 8.5, alternatively at least 9; preferably the pH is no greater than 12, alternatively no greater than 11.5, alternatively no greater than 11, alternatively no greater than 10.5. In one embodiment, the cooling water temperature is at least 30° C., alternatively at least 35° C., alternatively at least 40° C.; preferably the cooling water temperature is no greater than 70° C., alternatively no greater than 60° C.

The present invention is further directed to a method for controlling the growth of mycobacteria, especially *M. immunogenum*, associated with hypersensitivity pneumonitis (HP) in metalworking fluids using MIT biocide as a single-pack treatment, which has low odor, does not release or contain formaldehyde, does not contain metal salts (especially copper), and which is highly stable in alkaline metalworking fluids (pH>7). The biocide is substantially free of halogenated biocides, i.e., it contains less than 0.5% of such biocides, alternatively less than 0.1%, alternatively less than 100 ppm, alternatively less than 50 ppm. In some embodiments, the biocide is free of halogenated biocides. Treatment with MIT at 50 to 300 ppm is preferred, with 100-200 ppm more preferred, and 125-150 ppm most preferred. Control of mycobacteria is achieved for a minimum of 48 hours after dosing. Levels of mycobacteria are monitored in the fluid to confirm that the growth of mycobacteria has been suppressed after treatment The following examples provide supporting data for the concept of using 2-methyl-4-isothiazolin-3-one (MIT) biocide for the control of mycobacteria (gram positive, acid-fast bacteria) recently identified and recovered from in-use metalworking fluid system. Results of studies with laboratory and field samples have shown that MIT biocide displayed surprising efficacy in controlling growth of mycobacteria encountered in contaminated metalworking fluid systems, especially compared to known metalworking fluid biocides. In addition, use of MIT provides a one-pack, high pH stable biocide treatment which does not contain or release formaldehyde and which has no heavy metals, no solvent, and no odor.

Summary

Several commonly used biocides in the metalworking fluid industry were tested for their basic level of effectiveness versus pure cultures of *Mycobacterium* when using standard microbiological efficacy procedures; the Minimum Inhibitory Concentration (MIC) and Minimum Biocidal Concentration (MBC) tests. In these tests, all of the commercial biocides showed efficacy at levels below their typical maximum use rate to inhibit or kill the two strains of *Mycobacterium* which were evaluated. Based on these laboratory efficacy tests, it would be expected that all of these biocides would show good efficacy at their typical use rates in killing these organisms in contaminated samples from the field.

However, MIT provided unexpected results in controlling the growth of mixed populations of naturally occurring mycobacteria in all samples from six in-use and contaminated metalworking fluid systems. MIT outperformed all of the other commercial metalworking fluid biocides when used at their maximum recommended doses (including three isothiazolone products, a chlorophenolic, and a formaldehyde-releasing triazine biocide) in providing a minimum degree of efficacy (>90% kill) in all six samples of contaminated fluids received from the field.

Background

Metalworking fluids, also referred to as metal machining or metal cutting fluids, are used for cooling and lubricity in metalworking applications. Water-based metalworking fluids are susceptible to microbial contamination by various types of bacteria and fungi, as the fluids are recirculated in an open environment. Various types of gram-negative and gram-positive bacteria, yeasts, and molds are encountered. One specific type of gram-positive bacteria which has recently been identified and recovered in these fluids are members of the genus *Mycobacterium*, also referred to as mycobacteria.

Mycobacteria comprise a genus of bacteria, which are gram positive, contain mycolic acids in their cell walls, and respond positively to acid-fast staining using standard bacteriological procedures. These organisms have also been recently associated with the occurrence of specific health problems, known as "hypersensitivity pneumonitis" (HP), which may be encountered by individuals working in a metal machining or metalworking environment in which aerosols containing these bacteria may be present. *Mycobacterium immunogenum*, has recently been identified as a new species of mycobacteria in metalworking fluids associated with outbreaks of HP and continues to be recovered in additional fluid systems experiencing HP problems. A recent study using *M. immunogenum* in mixed populations of metalworking fluids showed the isothiazolone biocide (CMT/MIT) was more effective versus triazines, PCMC, and oxazolidine biocides for rapid kill at equivalent product concentrations (Selvaraju et al., 2005, Appl. Env. Microbiol, 71:542-546).

An improved method for controlling the growth of microorganisms in metalworking fluids was described in a recent patent by Rossmoore (U.S. Pat. No. 4,608,183) using combinations of isothiazolones and monocopper citrate (CMIT/MIT/MCC). The synergy and improved stability of the CMIT compound provided improved efficacy and performance in metalworking fluids.

A method to control the growth of mycobacteria, specifically *M. immunogenum*, associated with HP, by using the combination of dosing a CMIT/MIT product with MCC has been recently disclosed by Rossmoore (U.S. Pat. No. 6,951,618). High levels of copper citrate (500 ppm) were shown to improve the stability of the chlorinated isothiazolone (CMIT) which is the most active isothiazolone in the CMIT/MIT mixture, but which is subject to rapid degradation by nucleophilic compounds. However, use of high levels of copper in metalworking fluids are not always desired due to discoloration of the end use fluid, increased costs for disposal and waste treatment of the spent fluids, and potential corrosion and metal staining problems. The use of MIT alone as a single product treatment for control of mycobacteria was not disclosed by Rossmoore in this patent. Thus, there exists a need for biocides to provide control of mycobacteria, specifically *M. immunogenum*, in metalworking fluid systems, with improved stability without the use of adding high levels of added metals or dual product dosing.

EXAMPLES

Example 1

Improved Stability of MI Versus BIT and BNPD Biocides in a pH 9 Buffer Solution at 70° C.

Summary

Studies were conducted to determine the stability of MI (2-methyl-4-isothiazolin-3-one), BIT (1,2-benzisothiazolin-3-one) and BNPD (2-bromo-2-nitro-propane-1,3-diol) under high pH and high temperature conditions. MI demonstrated excellent stability in the pH 9 buffer at 70° C. after 56 days storage. There was no loss of MI over this time. BIT showed decreasing stability over the 56 day study with 32% loss of active ingredient at day 56. BNPD was completely degraded with 5 hours at pH 9 and 70° C.

Method pH 9 buffer containing 0.069 M boric acid, 0.017 M citric acid, 0.066 M sodium phosphate was prepared in distilled water. Biocide was dosed into the pH 9 buffer solution and stored at 70° C. in a heat block. The samples were examined for active ingredient concentration at the time points after 5 hours, and 1, 3, 7, 23, 30, 35 and 56 days. Initial biocide doses were 166 ppm MI, 199 ppm BIT and 150 ppm BNPD.

The samples were evaluated for active ingredient concentration via High Pressure Liquid Chromatography. Samples were taken from the heating blocks and allowed to cool to room temperature for 30 minutes. The samples were then diluted 1:20 in deionized water by adding 9.5 ml of deionized water to 0.5 grams of the samples in a 25 ml glass sample vial. The samples were mixed for 15 seconds and transferred to HPLC sample vials for analysis. Analytical variation for the HPLC method is ±10%.

Results

There was no loss of MI when stored at 70° C. over 56 days. BIT was less stable with 32% degraded at 70° C. BNPD stability was poor with almost immediate total degradation observed after 5 hours.

|         | Percent Remaining after: | | | | | | | |
|---------|---|---|---|---|---|---|---|---|
| Biocide | 0 | 5 hr | 1 day | 3 day | 7 day | 23 day | 30 day | 35 day | 56 day |
| MI      | 100 | 96 | 96 | 96 | 93 | 95 | 101 | 93 | 102 |
| BIT     | 100 | 98 | 97 | 94 | 92 | 86 | 71 | 63 | 68 |
| BNPD    | 100 | 0 | 0 | nt | nt | nt | nt | nt | nt | nt = not tested

Example 2

Improved Stability of MI Versus BIT with Various Oxidizing and Reducing Agents at pH 7 and pH 9

Summary

The stability of MI and BIT was evaluated in the presence of various redox agents in pH 7.0 and 9.0 buffer at 2 and 8 days. The results showed greater stability of MI versus BIT under various redox conditions and at elevated pH. Both biocides showed slight degradation with sodium bisulfite at pH 9, but were significantly degraded at pH 7.0. Bisulfite is a known deactivating agent for isothiazolones, especially at lower pH values.

Methods

Oxidizing agents (2 mM) included hydrogen peroxide ($H_2O_2$; 68 ppm), t-butyl hydrogen peroxide (t-BHP; 180 ppm), and potassium persulfate ($K_2O_8S_2$; 540 ppm). Reducing agents (2 mM) included iso-ascorbic acid (IAA; 352 ppm) and sodium bisulfite ($NaHSO_3$; 208 ppm). Biocides were tested at 1 mM concentrations, representing 115 ppm MI and 166 ppm BIT.

The pH 7.0 buffer contained 0.00426% monopotassium phosphate plus 0.019% magnesium chloride hexahydrate. The pH 9.0 buffer contained 0.0046 M hydrochloric acid plus 0.013 M borax. Stock solutions of the redox agents were prepared and added to aliquots of each buffer to give 2 mM concentrations. The biocides were then added to give 1 mM concentrations. The samples were stored at 25° C. and analyzed for biocide level by HPLC at 0, 2 and 8 days.

Results

The results showed greater stability of MI versus BIT under various redox conditions and at elevated pH. MI was more stable than BIT for all of the oxidants tested and only a minimal pH effect was seen at 8 days with hydrogen peroxide. Very little, if any, BIT remained after 8 days with all oxidants at pH 9. BIT also showed more degradation at higher pH versus pH 7, especially with hydrogen peroxide. MI showed better stability versus BIT against the ascorbic acid reducing agent and was not affected by pH. Both biocides showed slight degradation with sodium bisulfite at pH 9, but were significantly degraded at pH 7.0 within 2 days (a known deactivating agent for isothiazolones).

|             | % Remaining after 2 Days | | | | % Remaining after 8 Days | | | |
|-------------|------|------|------|------|------|------|------|------|
|             | MI | | BIT | | MI | | BIT | |
| Redox Agent | pH 7 | pH 9 | pH 7 | pH 9 | pH 7 | pH 9 | pH 7 | pH 9 |
| None        | 100 | 100 | 100 | 100 | 100 | 100 | 100 | 100 |
| $H_2O_2$    | 100 | 94 | 39 | 8 | 100 | 88 | 15 | 0 |
| t-BHP       | 99 | 98 | 43 | 38 | 102 | 96 | 8 | 6 |
| K-persulfate| 90 | 93 | 0 | 0 | 75 | 73 | 0 | 0 |
| IAA         | 100 | 105 | 89 | 77 | 96 | 103 | 86 | 75 |
| Na bisulfite| 29 | 70 | 38 | 82 | 26 | 78 | 28 | 77 |

*redox agents added at 2 mM and biocides added at 1 mM

Example 3

Improved Stability of MI Versus CMI and BIT Isothiazolones in Buffered Water at Various pH and Temperatures Summary Stability studies were conducted versus three isothiazolone in buffered deionized water at two different temperatures (22° and 50° C.). MI was shown to be the most stable with only slight loss of active at 50° C. and pH 12 after 90 days. BIT showed good stability up to pH 10 at both temperatures. CMI was the least stable of the isothiazolones tested and was most affected by increasing temperature.

Methods

Biocides were added to buffer solutions and stability was tested at 22° and 50° C. using HPLC to measure biocide concentration at 0 time, 21 days, 43 days, and 88-90 days. Biocide stability was determined in the following buffer solutions: pH2, 0.01M HCl; pH6, 0.1M $KH_2PO_4$; pH8, 0.025M borate; pH10, 0.025M borate; pH12, 0.05M $Na_2HPO_4$. Biocide concentrations tested were 100 ppm MI, 200 ppm BIT, 44 ppm CMI.

Results

Stability studies were conducted versus three isothiazolone in buffered water at two different temperatures (22° and 50° C.). MI was the most stable biocide tested, followed by BIT, with CMI the least stable over the range of conditions. MI showed excellent stability at room temperature up to pH 12. At 50° C., MI stability decreased slightly, but only at pH 12. BIT showed excellent stability at room temperature and 50° C. up to pH 10. Slight degradation occurred at pH 12 at both temperatures. CMI showed rapid and complete degradation at pH 10-12 at room temperature (22° C.) and poor stability at pH 6-12 at the higher temperature.

|         |     | Percent Remaining at: | | | | |
|---------|-----|------|------|------|-------|-------|
| Biocide | Day | pH 2 | pH 6 | pH 8 | pH 10 | pH 12 |
| | Biocide stability at 22° C. in buffered water. | | | | | |
| CMI     | 0   | 100 | 100 | 100 | 100 | 100 |
|         | 21  | 100 | 100 | 100 | 0 | 0 |
|         | 43  | 100 | 100 | 91 | 0 | 0 |
|         | 88  | 100 | 100 | 95 | 0 | 0 |
| BIT     | 0   | 100 | 100 | 100 | 100 | 100 |
|         | 21  | 97 | 100 | 98 | 100 | 69 |
|         | 43  | 83 | 86 | 77 | 85 | 55 |

-continued

| Biocide | Day | pH 2 | pH 6 | pH 8 | pH 10 | pH 12 |
|---------|-----|------|------|------|-------|-------|
|         | 88  | 95   | 100  | 84   | 96    | 63    |
| MI      | 0   | 100  | 100  | 100  | 100   | 100   |
|         | 21  | 104  | 100  | 100  | 100   | 98    |
|         | 43  | 98   | 94   | 95   | 89    | 93    |
|         | 88  | 100  | 100  | 100  | 100   | 100   |

Biocide stability at 50° C. in buffered water.

| Biocide | Day | pH 2 | pH 6 | pH 8 | pH 10 | pH 12 |
|---------|-----|------|------|------|-------|-------|
| CMI     | 0   | 100  | 100  | 100  | 100   | 100   |
|         | 21  | 100  | 100  | 15   | 0     | 0     |
|         | 43  | 93   | 65   | 0    | 0     | 0     |
|         | 88  | 100  | 30   | 0    | 0     | 0     |
| BIT     | 0   | 100  | 100  | 100  | 100   | 100   |
|         | 21  | 95   | 100  | 94   | 100   | 68    |
|         | 43  | 80   | 88   | 73   | 81    | 55    |
|         | 90  | 93   | 100  | 89   | 95    | 68    |
| MI      | 0   | 100  | 100  | 100  | 100   | 100   |
|         | 21  | 100  | 98   | 100  | 98    | 90    |
|         | 43  | 97   | 93   | 95   | 93    | 78    |
|         | 90  | 100  | 100  | 100  | 100   | 76    |

Example 4

Effective Levels of MI Versus Bacteria and Fungi

Summary

Minimum Inhibitory Concentration (MIC) studies with bacteria and fungi demonstrated that MI alone required significantly higher concentrations for efficacy compared to MI present in the 3:1 ratio CMI+MI combination product. In the CMI+MI combination, the level of antimicrobial activity is solely due to the chlorinated isothiazolone (CMI) and the level of MI present is significantly lower than the level of MI alone required for efficacy.

Methods

Minimum inhibitory concentration (MIC) studies were conducted to determine the lowest level of biocide required to inhibit growth of bacteria and fungi. Tests were conducted in 96-well microtiter plates. Biocides were added to growth media in the plates and serially diluted to obtain a range of concentrations. Bacterial tests were conducted in trypticase soy broth (TSB; pH 7) using an overnight inoculum added at $10^6$ colony forming units per ml. Samples were incubated at 25° C. for two days and the MIC value determined visually on a growth no-growth basis. Fungal tests were conducted in malt extract broth (MEB; pH 4.7) using an 5-7 day inoculum added at $10^4$ colony forming units per ml. Samples were incubated at 25° C. for 7 days and the MIC value determined as above.

Results

The MIC studies show that the level of MI required for efficacy is significantly (10-100×) greater than the MI level present in the 3:1 ratio CMI:MI combination product for control of both bacteria and fungi. The average MIC value for MI alone versus bacteria and fungi was 24 and 63 ppm MI alone, respectively; whereas, in the 3:1 combination the MI was present at only 0.56 and 0.34 ppm, respectively. Thus, the MI present in the combination biocide was significantly lower than that required from MI alone and the CMI component of the blended isothiazolone was solely responsible for the efficacy observed.

|  | MIC (ppm) | | Conc. of MI in the |
|---|---|---|---|
|  | MI | CMI + MI (3:1) | 3:1 CMI + MI Combination MIC |

Comparison of Minimum Inhibitory Concentration (MIC) Values for MI alone versus CMI + MI Combination versus Bacteria Bacteria

| Organism | MI | CMI+MI (3:1) | 3:1 Combination MIC |
|---|---|---|---|
| Alcaligenes faecalis | 28 | 2.5 | 0.63 |
| Citrobacter freundii | 25 | 0.8 | 0.20 |
| Citrobacter freundii | 41 | 0.8 | 0.20 |
| Enterobacter cloacae | 25 | 1.5 | 0.38 |
| Enterobacter aerogenes | 82 | 8.0 | 2.00 |
| Escherichia coli | 31 | 2.5 | 0.63 |
| Klebsiella pneumoniae | 12 | 0.4 | 0.10 |
| Proteus mirabilis | 21 | 0.8 | 0.20 |
| Pseudomonas aeruginosa | 15 | 2.5 | 0.63 |
| Pseudomonas aeruginosa | 25 | 2.5 | 0.63 |
| Pseudomonas fluorescens | 31 | 3.0 | 0.75 |
| Pseudomonas fluorescens | 16 | 2.5 | 0.63 |
| Pseudomonas oleovorans | 6 | 2.5 | 0.63 |
| Pseudomonas oleovorans | 6 | 1.2 | 0.30 |
| Pseudomonas putida | 13 | 3.0 | 0.75 |
| Shewanella putrefaciens | 13 | 1.2 | 0.30 |
| Average | 24 | 2.2 | 0.56 |
| MI: CMI + MI MIC Ratio | | 10.9 | |

Comparison of Minimum Inhibitory Concentration (MIC) Values for MI alone versus CMI + MI Combination versus Fungi Fungi

| Organism | MI | CMI+MI (3:1) | 3:1 Combination MIC |
|---|---|---|---|
| Acremonium strictum | 16 | 0.6 | 0.15 |
| Candida albicans | 100 | 1.5 | 0.38 |
| Field Isolate | 8 | 0.4 | 0.10 |
| Field Isolate | 21 | 0.2 | 0.05 |
| Field Isolate | 6 | 0.2 | 0.05 |
| Fusarium solani | 13 | 0.4 | 0.10 |
| Fusarium sp. | 25 | 0.4 | 0.10 |
| Geotrichum candidum | 250 | 7.0 | 1.75 |
| Rhodotorula rubra | 125 | 1.5 | 0.38 |
| Trichosporon sp. | 63 | 1.2 | 0.30 |
| Average | 63 | 1.3 | 0.34 |
| MI: CMI + MI MIC Ratio | | 46.8 | |

Example 5

Improved Efficacy of MI Versus BIT Against Bacteria and Fungi at Elevated pH Values Summary Minimum Inhibitory Concentration (MIC) studies with bacteria and fungi demonstrated that MI efficacy was not significantly affected by increasing pH (pH 9 vs. pH 7), whereas BIT was less effective for control of microbial growth under more alkaline conditions (pH 9). Based on these findings, MI would be a more desirable biocide for effective control of microorganisms under high pH conditions.

Methods

Minimum inhibitory concentration (MIC) studies were conducted to determine the lowest level of biocide required to inhibit growth of bacteria and fungi. Tests were conducted in 96-well microtiter plates. Biocides were added to growth media in the plates and serially diluted to obtain a range of concentrations. Tests were conducted in one-half strength trypticase soy broth (TSB; adjusted to pH 7.1 or pH 9.0). Bacteria and fungi were added to samples at $10^6$ colony forming units per ml and incubated at 30° C. for three days. MIC values were determined visually on a growth no-growth basis.

Results

Minimum Inhibitory Concentration (MIC) studies with bacteria and fungi demonstrated that MI efficacy was not significantly affected by increasing pH (pH 9 vs. pH 7), whereas BIT was less effective for control of microbial growth under more alkaline conditions (pH 9).

MIC values for MI showed no major difference in antimicrobial activity at pH 7.1 versus pH 9.0. Results at both pH values were generally identical, or within one well in the microtiter plate (equal to a 2× difference) which is the limit of resolution of the MIC test. None of the organisms tested with MI showed more than a 2× change in efficacy as a function of pH.

BIT, by comparison, showed significantly higher MIC values at pH 9.0 versus pH 7.1 for most of the bacteria and fungi tested. Eight of the nine organisms showed a pH effect with BIT, with MIC values from 4 to 30× higher at pH 9.0 versus pH 7.1.

These results demonstrate MI as a highly effective biocide for use in applications with elevated pH conditions.

| Organism And Strain Number | Minimum Inhibitory Concentration (ppm) | | | |
|---|---|---|---|---|
| | MI | | BIT | |
| | pH 7.1 | pH 9.0 | pH 7.1 | pH 9.0 |
| Aspergillus niger #128 | 100 | 100 | 50 | 200 |
| Aspergillus sp. #120 | 50 | 50 | 50 | 400 |
| Rhodotorula rubra #156 | 25 | 25 | <6.3 | 100 |
| Pseudomonas aeruginosa #13 | 12.5 | 6.3 | 50 | 200 |
| Pseudomonas pseudoalcaligenes #15 | 25 | 25 | 12.5 | 25 |
| Alcaligenes faecalis #93 | 3.2 | 6.3 | <1.6 | 6.3 |
| Alcaligenes xylosoxydans #95 | 12.5 | 25 | 6.3 | 25 |
| Pseudomonas diminuta #99 | 12.5 | 6.3 | 3.2 | 12.5 |
| Streptomyces sp. #130 | 3.2 | 3.2 | <1.6 | 3.2 |

Values in bold represent a 4× or greater increase in the MIC at pH 9.0 versus 7.1.

Example 6

Minimum Inhibitory Concentration (MIC) and Minimum Biocidal Concentration (MBC) Studies with Commercial Biocides Versus Pure Cultures of *Mycobacterium* in Standard Laboratory Media MIC and MBC studies were conducted to determine the basic efficacy of several commercial biocides typically used in metalworking fluids, for inhibition and killing of two strains of mycobacteria using standard media and laboratory procedures. Results showed that all commercial biocides demonstrated efficacy (both inhibition and killing) of both strains at levels below their maximum recommended use level. This indicates that these biocide possess the inherent antimicrobial efficacy against strains of mycobacteria, when tested in the absence of other bacteria and using standard laboratory media.

The lowest concentration of microbicide required to inhibit bacteria was determined by a high resolution MIC test. Varying amounts of each microbicide were added to media in a 96-well microtiter plate. The media used for the MIC tests was 10% Trypicase Soy Broth (1/10× TSB). Ten-fold serial dilutions were performed on a Biomek 2000 Workstation to obtain a range of closely spaced concentrations of microbicides. A cell suspension of stationary phase microorganisms, adjusted to provide $10^6$ colony forming units (CFU)/mL in each well for bacteria was added to the microtiter plate. The microtiter plates were incubated for 24 hours at 30° C. for *Mycobacterium immunogenum* and 37° C. for *Mycobacterium chelonae*. The presence or absence of microbial growth was determined by measuring the turbidity in each well using a Thermomax microplate reader set at an absorbance of 650 nm. The lowest concentration of compound in which no growth was observed was considered the MIC value for the microbicide. The MIC value for each microbicide was determined from the average of four determinations for bacteria.

Bacterial strains tested included *Mycobacterium chelonae* (ATCC 14472) and *Mycobacterium immunogenum* (ATCC 700505). Mycobacterial cultures were grown overnight at 30° C. (*M. immunogenum*) or 37° C. (*M. chelonae*), in a rotary shaking bath in Middlebrook 7H10 Agar with Middlebrook enrichment. A 1:20 dilution of the overnight culture was made into the appropriate test media and inoculated to give a final concentration of $10^6$ to $10^7$ CFU/ml.

MBC tests were conducted by transferring samples from the MIC test samples into fresh media and observing for growth of the culture. Growth was determined as above. In this test using Biomek 2000 Workstation, 10 µl samples taken from the 96-well MIC plates were placed in 190 ml of fresh growth media to determine the number of surviving organisms for the same gradient of biocide concentrations. These plates were incubated and read in the same fashion as the MIC plates. The lowest level of biocide from the MIC plates that showed no survivors upon transfer to fresh media after 2 days was considered the MBC.

Results shown in Table 1 demonstrate that all the commercial biocides demonstrated efficacy (both inhibition and killing) of both strains at levels less than their maximum recommended use level. Based on these data, it would be expected that these biocides should all be effective against similar organism encountered in actual metalworking fluid samples from the field.

TABLE 1

Minimum Inhibitory Concentration (MIC) and Minimum Biocidal Concentration (MBC) of Various Biocides Against Pure Cultures Strains of *Mycobacterium*

| Biocide | Maximum Use Level (ppm active) | Minimum Inhibitory Concentration (ppm active) | | Minimum Biocidal Concentration (ppm active) | |
|---|---|---|---|---|---|
| | | M. chelonae | M. immunogenum | M. chelonae | M. immunogenum |
| CMIT/MIT | 17.5 | 2.9 | 3.0 | 3.0 | 3.0 |
| CMIT/MIT/MCC | 17.5 | 0.8 | 1.1 | 0.8 | 1.1 |
| MIT | 150 | 15 | 50 | 40 | 84 |

TABLE 1-continued

Minimum Inhibitory Concentration (MIC) and Minimum Biocidal Concentration (MBC) of Various Biocides Against Pure Cultures Strains of *Mycobacterium*

| Biocide | Maximum Use Level (ppm active) | Minimum Inhibitory Concentration (ppm active) | | Minimum Biocidal Concentration (ppm active) | |
|---|---|---|---|---|---|
| | | M. chelonae | M. immunogenum | M. chelonae | M. immunogenum |
| BIT | 340 | 63 | 113 | 75 | 188 |
| Triazine | 1180 | 43 | 39 | 314 | 314 |
| Oxazolidine | 1560 | 42 | 38 | 34 | 836 |
| PCMC | 3450 | 20 | 35 | 60 | 75 |

Example 7

Comparison of Biocide Efficacy at the Maximum Recommended Dose Levels for Eradication and Control of Mycobacteria in Contaminated Samples of Metalworking Fluids from In-Use Systems A comparative study was conducted evaluating six metalworking fluid biocides versus natural, resident populations of *Mycobacterium* from six in-use metalworking fluids. CMIT/MIT, CMIT/MIT/MCC, MIT, BIT, triazine, and PCMC microbicides were tested under controlled laboratory conditions to determine their efficacy at the maximum manufacturer's recommended dose rate (Table 2). The metalworking fluids were known to contain high levels of mycobacteria prior to dosing with biocides. Samples were then dosed with biocides, incubated with agitation at room temperature and viable mycobacteria counts determined after 48 hours by plating onto Middlebrook 7H10 medium, with Tween 80, glycerin, cyclohexamide, chloramphenicol, and gentamycin to suppress the growth of unwanted microorganisms.

The comparative efficacy (log kill) of the various biocides dosed at 100% of the manufacturer's maximum recommended treatment rate are shown in Table 3. MIT was the only biocide which provided at least a one-log reduction (90% kill) in each of the six metalworking fluids (Table 4). MIT was also the only biocide which provided at least a two-log reduction (99% kill) in five of the six fluids tested. PCMC was effective in five fluids tested with at least a 90% kill and in four fluids with a minimum 99% kill. CMIT/MIT and CMIT/MIT/MCC were only effective in four of the six fluids tested at these kill rates. Triazine and BIT biocides did not show efficacy in any of the fluids tested.

These results showed MIT as surprisingly effective for controlling the growth of mycobacteria in naturally contaminated metalworking fluids at the maximum recommended dose levels, especially since all of these biocides previously demonstrated efficacy against pure cultures of these organisms in laboratory studies at lower levels. MIT significantly outperformed all other biocides, including CMIT/MIT/MCC, previously reported by Rossmoore (U.S. Pat. No. 6,951,618) as a highly effective biocide versus mycobacteria. However, the MIT treatment method does not require the use of two products and does not require high levels of copper salts, which add color to fluids and poses potential corrosion, metal staining and waste treatment problems.

TABLE 2

Biocides tested and dose levels for in-use eradication efficacy studies versus mycobacteria in contaminated field samples.

| Biocide Tested | 50% of Maximum Dose | 100% of Maximum Dose |
|---|---|---|
| CMIT/MIT (14% active KATHON ™ 886 MW) | 9 ppm | 17.5 ppm |
| CMIT/MIT/MCC (1.5% active KATHON ™ CC) | 9 ppm | 17.5 ppm |
| MIT (50% active KORDEK ™ LX 5000) | 75 ppm | 150 ppm |
| Triazine (78.5% active GROTAN ™) | 588 ppm | 1,180 ppm |
| PCMC (46% active PREVENTOL ™ CMK) | 1725 ppm | 3,450 ppm |
| BIT (19% active PROXEL ™ GXL) | 171 ppm | 342 ppm |

Biocides are given as active ingredient dose levels.
See previous text for specific chemical composition of the actives.
KATHON ™ and KORDEK ™ are registered trademarks of the Rohm and Haas Company.
GROTAN ™ is a registered trademark of the Troy Chemical Company, Ltd.
PREVENTOL ™ is a registered trademark of the Lanxess Corporation.
PROXEL ™ is a registered trademark of the Arch Corporation.

TABLE 3

Log reduction of mycobacteria counts in naturally contaminated metalworking fluids 48 hours after adding biocides at 100% of the recommended maximum dose level.

| Biocide | Log Reduction in Mycobacterial Counts versus Control (no biocide) | | | | | |
|---|---|---|---|---|---|---|
| | Fluid 1 | Fluid 2 | Fluid 3 | Fluid 4 | Fluid 5 | Fluid 6 |
| MIT | 5.88 | 5.00 | 2.00 | 3.64 | 1.90 | 3.88 |
| CMIT/MIT | 4.97 | 5.00 | 0.00 | 3.24 | 0.09 | 3.88 |
| CMIT/MIT/MCC | 5.57 | 5.00 | 0.00 | 3.54 | 0.00 | 3.88 |

TABLE 3-continued

Log reduction of mycobacteria counts in naturally contaminated metalworking fluids 48 hours after adding biocides at 100% of the recommended maximum dose level.

| Biocide | Log Reduction in Mycobacterial Counts versus Control (no biocide) | | | | | |
|---|---|---|---|---|---|---|
| | Fluid 1 | Fluid 2 | Fluid 3 | Fluid 4 | Fluid 5 | Fluid 6 |
| Triazine | 0.00 | 0.12 | 0.00 | 0.00 | 0.00 | 0.00 |
| BIT | 0.00 | 0.00 | 0.60 | 0.00 | 0.06 | 0.00 |
| PCMC | 5.88 | 5.00 | 1.00 | 5.24 | 0.90 | 3.88 |
| Untreated Control* (Initial Count) | $1.5 \times 10^6$ | $2.0 \times 10^5$ | $1.0 \times 10^6$ | $3.5 \times 10^5$ | $8.0 \times 10^5$ | $1.5 \times 10^4$ |
| Untreated Control* (48 hour count) | $3.5 \times 10^6$ | $6.0 \times 10^5$ | $3.0 \times 10^6$ | $5.0 \times 10^5$ | $1.0 \times 10^6$ | $7.5 \times 10^4$ |

*Mycobacterial counts (per ml) in untreated control samples

TABLE 4

Efficacy of six biocides versus mycobacteria in naturally contaminated fluids 48 hours after doing at 100% of recommended maximum levels.

| Biocide | No. of Fluids with ≧90% Kill (1-log reduction) | No. of Fluids with ≧99% Kill (2-log reduction) |
|---|---|---|
| MIT | 6 | 5 |
| CMIT/MIT | 4 | 4 |
| CMIT/MIT/MCC | 4 | 4 |
| PCMC | 5 | 4 |
| Triazine | 0 | 0 |
| BIT | 0 | 0 |

Example 8

Comparison of Biocide Efficacy at 50% of the Maximum Recommended Dose Levels for Eradication and Control of Mycobacteria in Contaminated Samples of Metalworking Fluids from In-Use Systems The six metalworking fluid samples containing mycobacteria study from Example 7, were also tested using the same biocides with dosing at 50% of the maximum manufacturer's recommended rate (Table 2) under the same conditions. These metalworking fluids were known to contain high levels of mycobacteria prior to dosing with biocides. Samples were then dosed with biocides, incubated with agitation at room temperature and viable mycobacteria counts determined after 48 hours by plating onto Middlebrook 7H10 medium, with Tween 80, glycerin, cyclohexamide, chloramphenicol, and gentamycin to suppress the growth of unwanted microorganisms.

The efficacy (log kill) data for dosing at 50% of the maximum treatment rate are shown in Table 5. MIT and CMIT/MIT/MCC were the only biocide which provided at least a one-log reduction (90% kill) in four of the six fluids and at least a two-log reduction (99% kill) in three of the six fluids tested (Table 6). CMIT/MIT achieved a minimum 90% to 99% kill in only three fluids. PCMC provided ≧90% kill in three fluids and achieved a ≧99% kill in only two fluids. Triazine and BIT biocides did not show efficacy in any of the six fluids tested.

These results showed MIT as surprisingly effective for controlling the growth of mycobacteria in naturally contaminated metalworking fluids even when dosed at 50% of the maximum recommended treatment level, especially since all of these biocides previously demonstrated efficacy against pure cultures of these organisms in laboratory studies at low levels. At one-half the recommended use rate, MIT provided similar efficacy compared to CMIT/MIT/MCC biocide, previously reported by Rossmoore (U.S. Pat. No. 6,951,618) as a highly effective biocide versus mycobacteria. However, the MIT treatment method does not require the use of two products and does not require high levels of copper salts, which add color to fluids and poses potential corrosion, metal staining, and waste treatment problems.

TABLE 5

Log reduction of mycobacteria counts in naturally contaminated metalworking fluids 48 hours after adding biocides at 50% of the recommended maximum dose level.

| Biocide | Log Reduction in Mycobacterial Counts versus Control (no biocide) | | | | | |
|---|---|---|---|---|---|---|
| | Fluid 1 | Fluid 2 | Fluid 3 | Fluid 4 | Fluid 5 | Fluid 6 |
| MIT | 3.48 | 3.80 | 0.00 | 2.00 | 0.06 | 1.78 |
| CMIT/MIT | 2.00 | 2.30 | 0.00 | 0.77 | 0.00 | 2.00 |
| CMIT/MIT/MCC | 1.88 | 5.00 | 0.00 | 2.54 | 0.00 | 2.18 |
| Triazine | 0.00 | 0.00 | 0.00 | 0.00 | 0.06 | 0.00 |
| BIT | 0.00 | 0.00 | 0.00 | 0.00 | 0.00 | 0.00 |
| PCMC | 0.00 | 1.00 | 0.00 | 5.24 | 0.51 | 3.88 |

TABLE 5-continued

Log reduction of mycobacteria counts in naturally contaminated metalworking fluids 48 hours after adding biocides at 50% of the recommended maximum dose level.

| | Log Reduction in Mycobacterial Counts versus Control (no biocide) | | | | | |
|---|---|---|---|---|---|---|
| Biocide | Fluid 1 | Fluid 2 | Fluid 3 | Fluid 4 | Fluid 5 | Fluid 6 |
| Untreated Control* (Initial Count) | $1.5 \times 10^6$ | $2.0 \times 10^5$ | $1.0 \times 10^6$ | $3.5 \times 10^5$ | $8.0 \times 10^5$ | $1.5 \times 10^4$ |
| Untreated Control* (48 hour count) | $3.5 \times 10^6$ | $6.0 \times 10^5$ | $3.0 \times 10^6$ | $5.0 \times 10^5$ | $1.0 \times 10^6$ | $7.5 \times 10^4$ |

*Mycobacterial counts (per ml) in untreated control samples

TABLE 6

Efficacy of six biocides versus mycobacteria in naturally contaminated fluids 48 hours after dosing at 50% of recommended maximum levels.

| Biocide | No. of Fluids with ≧90% Kill (1-log reduction) | No. of Fluids with ≧99% Kill (2-log reduction) |
|---|---|---|
| MIT | 4 | 3 |
| CMIT/MIT | 3 | 3 |
| CMIT/MIT/MCC | 4 | 3 |
| PCMC | 3 | 2 |
| Triazine | 0 | 0 |
| BIT | 0 | 0 |

Example 9

Comparison of Stability of MIT Versus CMIT (with and Without MCC) in Aggressive Metalworking Fluids Stability studies were conducted in three high pH metalworking fluid use dilutions to compare the persistence of MIT biocide versus CMIT biocide, tested alone and in combination with MCC). Aliquots of the use-diluted fluids were dosed with 17.5 ppm active CMIT/MIT and CMIT/MIT/MCC and stored at 25° C. Biocide concentrations were determined at time zero and weekly using high performance liquid chromatography (HPLC) analysis.

Results showed that MIT alone retained greater than 90% of the biocide active after 3-4 weeks in all three of the high pH use-diluted fluids (Table 7). By contrast, CMIT alone rapidly degraded in the three fluids with none remaining after 3-4 weeks. Addition of 300 ppm MCC improved CMIT stability moderately, but none of the fluid had more than 16% of the biocide remaining after 3-4 weeks.

These results clearly demonstrate the superior stability of MIT biocide relative to the combination of CMIT plus MCC in typical (high pH) metalworking fluid use dilutions. Rossmoore (U.S. Pat. No. 6,951,618) previously reported MCC as an effective stabilizer to prevent degradation of CMIT in aggressive fluids; however, this effect was not observed to be long-lived or highly effective for extended periods in the fluids tested herein. Thus, MIT was shown to be not only the most effective biocide for control of mycobacteria in metalworking fluids, it was also shown to be the most stable isothiazolone biocide for long-term persistence for microbial control in aggressive fluids.

TABLE 7

Stability of CMIT versus MIT in end-use dilutions of metalworking fluids.

| Fluid Type | Time | % CMIT Remaining (without MCC) | % CMIT Remaining (with MCC) | % MIT Remaining |
|---|---|---|---|---|
| Soluble Fluid 1 (pH 9.2) | 2 wk | 28 | 38 | 95 |
| | 4 wk | 10 | 18 | 100 |
| Synthetic Fluid 2 (pH 9.4) | 1 wk | 13 | 42 | 92 |
| | 3 wk | 0* | 0 | 94 |
| Soluble Fluid 3 (pH 9.3) | 2 wk | 25 | 35 | 95 |
| | 4 wk | 0 | 16 | 100 |

CMIT added at 11-13 ppm
MCC added at 300 ppm
MIT added at 3.6-4.3 ppm
*= none detected (<0.8 ppm)
Analytical precision was +/−10%.

The invention claimed is:

1. A method for treating water in a closed cooling system, having a pH from 9 to 10.5 and a temperature of at least 35° C. and no more than 60° C., by adding a composition comprising 2-methyl-4-isothiazolin-3-one; wherein said composition is substantially free of metal ions non-aqueous solvents, volatile organic compounds and halogenated biocides; wherein metal ions, non-aqueous solvents, volatile organic compounds and halogenated biocides are not added separately to the water; and wherein 2-methyl-4-isothiazolin-3-one is present in an amount sufficient to produce in the water a 2-methyl-4-isothiazolin-3-one concentration from 15 ppm to 500 ppm to control the growth of microorganisms in said water.

2. The method of claim 1 in which the concentration of 2-methyl-4-isothiazolin-3-one is from 25 ppm to 300 ppm.

3. The method of claim 2 in which the water is substantially free of biocides other than 2-methyl-4-isothiazolin-3-one.

4. The method of claim 3 in which the concentration of 2-methyl-4-isothiazolin-3-one is from 30 ppm to 200 ppm.

5. A method for controlling the growth of mycobacteria in metalworking fluids; said method comprising adding 50 to 300 ppm of a 2-methyl-4-isothiazolin-3-one composition which does not contain metal salts to a metalworking fluid having a pH from 8 to 12; wherein the fluid is substantially free of halogenated biocides.

* * * * *